United States Patent [19]

Katou

[11] Patent Number: 5,502,521
[45] Date of Patent: Mar. 26, 1996

[54] OPHTHALMOMETRIC APPARATUS

[75] Inventor: Kouki Katou, Anjo, Japan

[73] Assignee: Nidek Co., Ltd., Japan

[21] Appl. No.: 223,298

[22] Filed: Apr. 26, 1994

[30] Foreign Application Priority Data

Apr. 30, 1993 [JP] Japan .................................. 5-128356
May 31, 1993 [JP] Japan .................................. 5-154419

[51] Int. Cl.$^6$ ............................... A61B 3/10; A61B 3/14
[52] U.S. Cl. ......................... 351/221; 351/208; 351/211
[58] Field of Search .................................. 351/200, 208, 351/211, 213, 221, 205

[56] References Cited

U.S. PATENT DOCUMENTS 5,101,826   4/1992   Katsuragi .................................. 351/208

FOREIGN PATENT DOCUMENTS

| 63-139529 | 6/1988  | Japan . |         |
|-----------|---------|---------|---------|
| 2-88038   | 3/1990  | Japan . |         |
| 3-5810    | 1/1991  | Japan . |         |
| 4-141135  | 5/1992  | Japan . |         |
| 5-42107   | 2/1993  | Japan . |         |
| 5-293084  | 11/1993 | Japan . |         |
| 6-63020   | 3/1994  | Japan   | 351/221 |

*Primary Examiner*—William L. Sikes
*Assistant Examiner*—Huy Mai
*Attorney, Agent, or Firm*—Parkhurst, Wendel & Rossi

[57] ABSTRACT

An ophthalmometric apparatus comprising an eyeball observing device for observing the front part of the eyeball and a measuring unit moving device for moving a measuring unit relative to the eyeball, characterized by: a first optical index forming system that projects a light beam along the optical axis of the eyeball observing device to form a first alignment index in the eyeball; a first optical index detecting system that detects the position of the first alignment index on the basis of the light that travels along the optical axis of the eyeball observing device; a second optical index forming system that projects a light beam on the eyeball along an optical axis inclined at an angle to the optical axis of the eyeball observing device to form a second alignment index in the eyeball; a second optical index detecting system that detects the position of the second alignment index and has an optical axis in a substantially mirror image relation with the optical axis of the second optical index forming system with respect to the optical axis of the eyeball observing device; a correction calculating device that calculates distance information about the distance between the eyeball and the eyeball observing device represented by the output of the second optical index detecting system, on the basis of the output of the first optical index detecting system, and a display device that displays distance information provided by the correction calculating device and representing the distance between the eyeball and the eyeball observing device in the observation field of the eyeball observing device.

17 Claims, 4 Drawing Sheets

OPHTHALMOMETRIC APPARATUS

BACKGROUND OF THE INVENTION

1. Field of the Invention

The present invention relates to an ophthalmometric apparatus, such as a noncontact intraocular pressure measuring apparatus or an objective ophthalmometer, and, more specifically, to an optical alignment system for an ophthalmometric apparatus.

2. Description of the Related Art

When examining the eyeball with an ophthalmometric apparatus, such as a noncontact intraocular pressure measuring apparatus or an objective ophthalmometer, the vertical and horizontal positions of the ophthalmometric apparatus relative to the eye and the operating distance between the ophthalmometric apparatus and the eye must be adjusted for alignment.

The applicant of the present patent application proposed previously a novel alignment adjusting system for an ophthalmometric apparatus in Japanese Patent Application No. Hei 4-122562 (Title of the invention: Ophthalmometer). An optical system described as a preferred embodiment of the invention in the specification comprises a first optical index detector that forms a" position index for the adjustment of the vertical and horizontal positions of the measuring system, projects the index and detects the same, and a second optical index detector that forms a distance index, projects an alignment light beam obliquely, and receives the alignment light beam at a position in mirror image relation with the position from which the alignment light beam is projected. A graphic mark (distance mark) represented by the output of the second index detector is displayed on a monitor display to provide information for adjustment.

In this previously proposed optical system, the accuracy of the detecting operation of the second index detector is affected delicately by the horizontal position of the eye relative to the second index detector, and the data acquired by the second index detector includes errors unless the horizontal position of the eye relative to the second index detector is adjusted accurately.

Furthermore, since the eye never remains stationary and keeps slight movement, the vertical and horizontal positions of the eye relative to the second index detector may change during the adjustment of the operating distance after the adjustment of the vertical and horizontal positions of the eye. In such a case, the adjustment of the vertical and horizontal positions of the eye relative to the second index detector must be carried out again. Thus, the previously proposed optical system requires a very troublesome operation.

SUMMARY OF THE INVENTION

The present invention has been made in view of the foregoing disadvantages of the known ophthalmometric apparatus and it is therefore an object of the present invention to provide an ophthalmometric apparatus capable of being easily operated for operating distance adjustment, and vertical and horizontal positional adjustment without being affected by operating distance adjustment.

With the foregoing object in view, the present invention provides an ophthalmometric apparatus comprising an eyeball observing means for observing the front part of the eyeball, a measuring means, and a measuring means moving means for moving the measuring means relative to the eyeball, the improvement comprising a first optical index forming system that projects a light beam along the optical axis of the eyeball observing means to form a first alignment index in the eyeball, a first optical index detecting system that detects the position of the first index on the basis of the light that travels along the optical axis of the eyeball observing means, a second optical index forming system that projects a light beam on the eyeball along an optical axis inclined at an angle to the optical axis of the eyeball observing means to form a second alignment index in the eyeball, a second optical index detecting system that detects the position of the second index, and has an optical axis in a substantially mirror image relation with the optical axis of the second optical index forming system with respect to the optical axis of the eyeball observing means, a correction calculating means that calculates distance information about the distance between the eyeball and the eyeball observing means represented by the output of the second optical index detecting system, on the basis of the output of the first optical index detecting system, and a display means that displays distance information provided by the correction calculating means and representing the distance between the eyeball and the eyeball observing means in the observation field of the eyeball observing means.

BRIEF DESCRIPTION OF THE DRAWINGS

The above and other objects, features and advantages of the present invention will become more apparent from the following description taken in connection with the accompanying drawings, in which.

DESCRIPTION OF THE PREFERRED EMBODIMENTS

An ophthalmometric apparatus in a preferred embodiment according to the present invention as applied to a noncontact intraocular pressure measuring apparatus will be described hereinafter.

Figure 1:
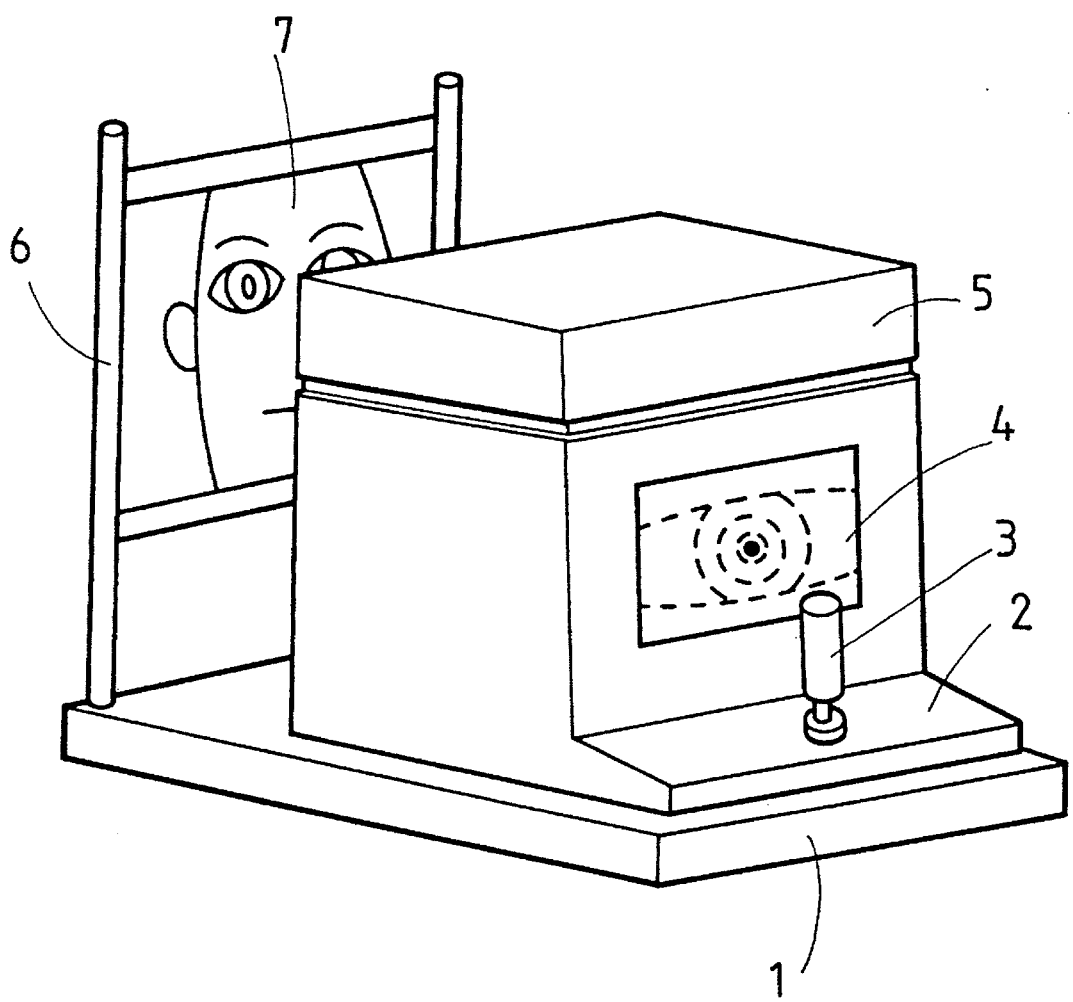
FIG. 1 is a perspective view of a noncontact intraocular pressure measuring apparatus, i.e., an ophthalmometric apparatus, in a preferred embodiment according to the present invention.

Referring to FIG. 1, a noncontact intraocular pressure measuring apparatus embodying the present invention comprises a base 1, a main unit 2 mounted on the base 1 for sliding movement in vertical and horizontal directions on the base 1, a housing 5 containing a measuring system and the like, mounted on the main unit 2, and a frame 6 for fixedly holding the head 7 of an examinee. An operating lever 3 is operated to move the main unit 2 on the base 1. A picture of the eye front of the eyeball of the examinee is displayed on a monitor display 4. The principal systems of the noncontact intraocular pressure measuring apparatus will be individually described hereinafter, in which the description of the measuring system will be omitted because the measuring system is of a well-known type.

Optical Alignment System

Figure 2:
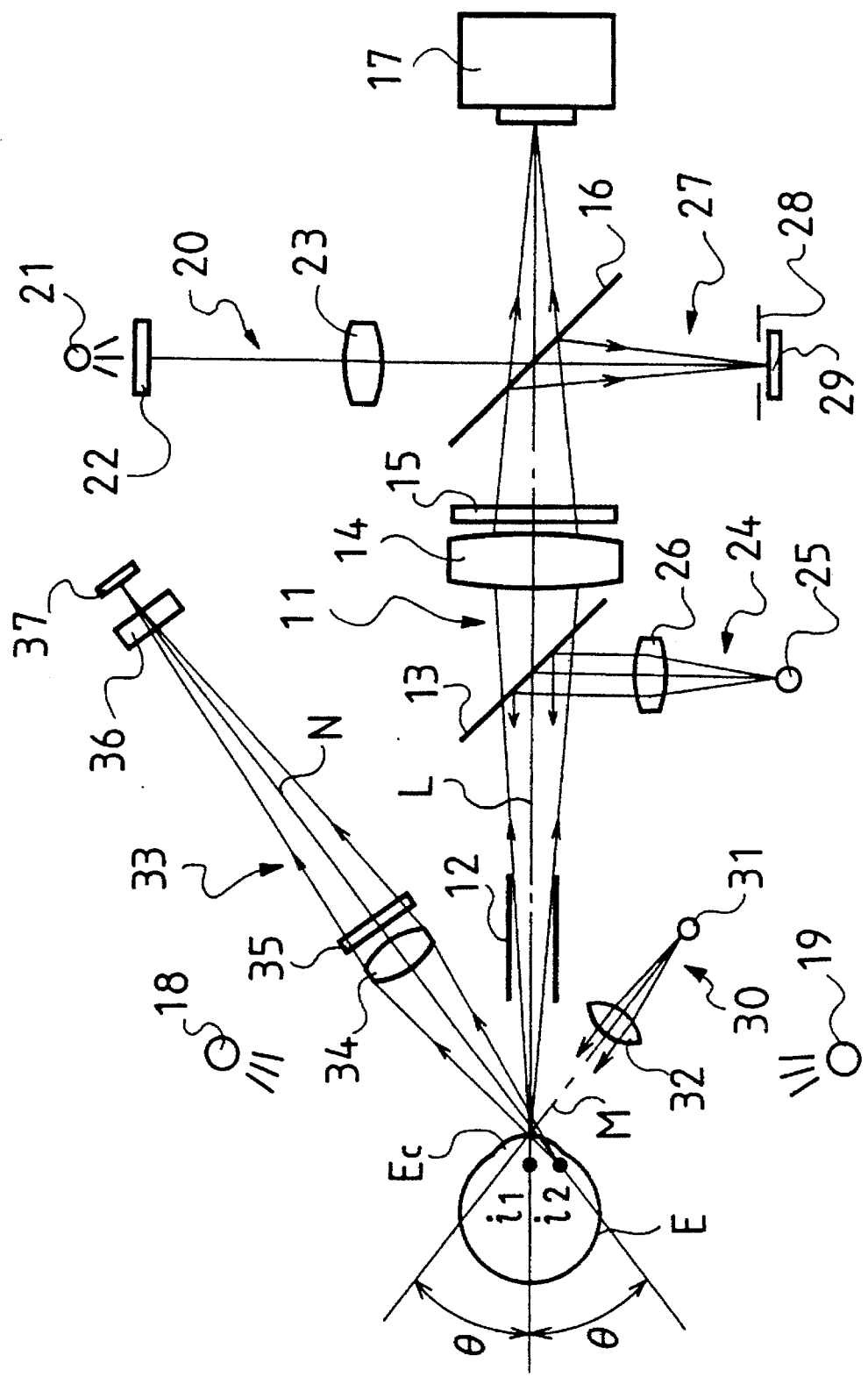
FIG. 2 is a diagrammatic view of an optical alignment system included in the noncontact intraocular pressure measuring apparatus of FIG. 1.

In FIG. 2 showing an optical alignment system included in the noncontact intraocular pressure measuring apparatus, indicated at E is the eyeball of an examinee, and at Ec is the cornea of the eyeball E. The optical alignment system comprises an optical observation system 11, an optical reticle projecting system 20, an optical front index projecting system 24, an optical front index detecting system 27, an optical distance index projecting system 30, and an optical distance index detecting system 33.

Optical Observation System

The optical observation system 11 is provided with a nozzle 12 for blowing out a gas for distorting the cornea. The nozzle 12 is disposed with its axis in alignment with the optical axis L of the optical observation system 11. A half mirror 13, an objective lens 14, a filter 15, a half mirror 16 and a TV camera 17 are arranged in that order on the optical axis L. The filter 15 transmits the light emitted by a light source 25 and absorbs the light emitted by a light source 31 to prevent the reflection of an index i2 in the TV camera and the detection of the index i2 by a two-dimensional position detecting device 29. Illuminating light sources 18 and 19 emit near infrared rays to illuminate the eyeball.

The eyeball E is illuminated by the near infrared rays emitted by the illuminating light sources 18 and 19. Light rays reflected by the eyeball E is transmitted through the half mirror 13, the filter 15 and the half mirror 16 and is focused by the objective lens 14 to form a front image of the eyeball E on the image plane of the TV camera 17.

Optical Reticle Projection System

The optical reticle projection system 20 comprises a light source 21, a reticle plate 22 and a projection lens 23. The light source 21 illuminates the reticle plate 22 to project the image of a reticle formed on the reticle plate 22. The image of the reticle is reflected by the half mirror 16 and is focused by the projection lens 23 on the image plane of the TV camera 17 so that the image of the reticle and that of the eyeball E are superposed on the image plane of the TV camera 17. When the measuring system and the eyeball E are aligned with respect to vertical and horizontal positions, the image of the reticle is in a specific positional relation with an index 11.

Optical Front Index Projection System

The optical front index projection system 24 comprises a light source 25 that projects light of a wavelength nearly equal to those of the light emitted by the illuminating light sources 18 and 19, and a projector lens 28. The light source 25 has an infrared-emitting diode, i.e., a LED that emits near infrared rays. The frequency of the near infrared rays emitted by the light source 25 is modulated by a predetermined modulating signal to prevent noise in the light reflected by the cornea and falling on the optical front index detecting system 27 attributable to the illuminating light emitted by the illuminating light sources 18 and 19. The light emitted by the light source 25 is collimated by the projector lens 26. The collimated light is reflected by the half mirror 13 so as to travel along the optical axis L through the nozzle 12 and fall on the cornea Ec. The light specularly reflected by the cornea Ec form the index 11, i.e., a virtual image of the light source 25. Part of the light reflected by the specular reflection of the cornea Ec travels through the nozzle 12 and is superposed over the front image of the eyeball E on the image plane of the TV camera 17 by the optical observation system 11.

Optical Front Index Detecting System

The optical front index detecting system 27 comprises a field stop 28 and a two-dimensional position detecting device 29, i.e., a sensor such as a CCD, a PSD or the like. Part of the light emitted by the light source 25 of the optical front index projection system 24 and specularly reflected by the cornea Ec is reflected toward the optical front index detecting system 27 by the half mirror 16. The fieldstop 28 has an aperture having a diameter that allows only the light flux passing an area limited by the nozzle 12 to fall on the two-dimensional position detecting device 29 and intercepts unwanted light. The output signal of the two-dimensional position detecting device 29 provided after receiving the light representing the index 11 is processed by a well-known signal processing procedure to determine the deviation of the image of the eyeball E from a correct position, i.e., the coordinates $\Delta x$ and $\Delta y$ of the position of the image of the eyeball E on an orthogonal coordinate system having its origin at the correct position, where $\Delta x$ is the horizontal displacement and $\Delta y$ is the vertical displacement of the image of the eyeball E from the correct position. The position of the main unit 2 relative to the eyeball E is adjusted so that the displacements $\Delta x$ and $\Delta y$ are within predetermined ranges, respectively. The horizontal displacement $\Delta x$ is used for distance detection, which will be described later.

Optical Distance Index Projection System

The optical distance index projection system 30 has an optical axis M intersects the optical axis L at an angle $\theta$ at a position on the optical axis L at an operating distance from the nozzle 12. The angle $\theta$ is in the range of 20° to 40°. The optical distance index projection system comprises a light source 31 that emits light of a wavelength different from that of the light emitted by the light source 25, and a projector lens 32, which are arranged on the optical axis M. The light emitted by the light source 31 is collimated by the projector lens 32, travels along the optical axis M and falls obliquely on the cornea Ec. The light specularly reflected by the cornea Ec forms the index i2, i.e., a virtual image of the light source 31.

Optical Distance Index Detecting System

The optical distance index detecting system 33 has an optical axis N. The optical axes M and N intersect in a point on the optical axis L and are symmetrical with respect to the optical axis L. The optical distance index detecting system 33 comprises a lens 34, a filter 35, a cylindrical lens 36 and a linear position detecting device 37, which are arranged along the optical axis N. The filter 35 transmits the light emitted by the light source 31 and absorbs the light emitted by the illuminating light source 18 and 19 to prevent the reflection of the image of the index 11 on the linear position detecting device 37 and noise attributable to the light emitted by the illuminating light sources 18 and 19.

The light representing the index i2 travels through the filter 35 and the cylindrical lens 36, and is focused on the image plane of the linear position detecting device 37 by the lens 34. Since the cylindrical lens 36 has a positive refractive power in a vertical plane, the light representing the index i2 falls on the image plane of the linear position detecting device 37 even if the eyeball E moves vertically. The image of the index i2 formed on the image plane of the linear position detecting device 37 by the lens 34 moves on the linear position detecting device 37 when the eyeball E moves along the optical axis L. The output signal of the linear position detecting device 37 is processed by a well-known signal processing procedure to determine the displacement Δ z of the image of the index i2 from a correct position where the image of the index i2 is formed when the eyeball E is positioned correctly in respect of the vertical and horizontal positions and the operating distance relative to the noncontact intraocular pressure measuring apparatus.

Signal Processing System

Figure 3:
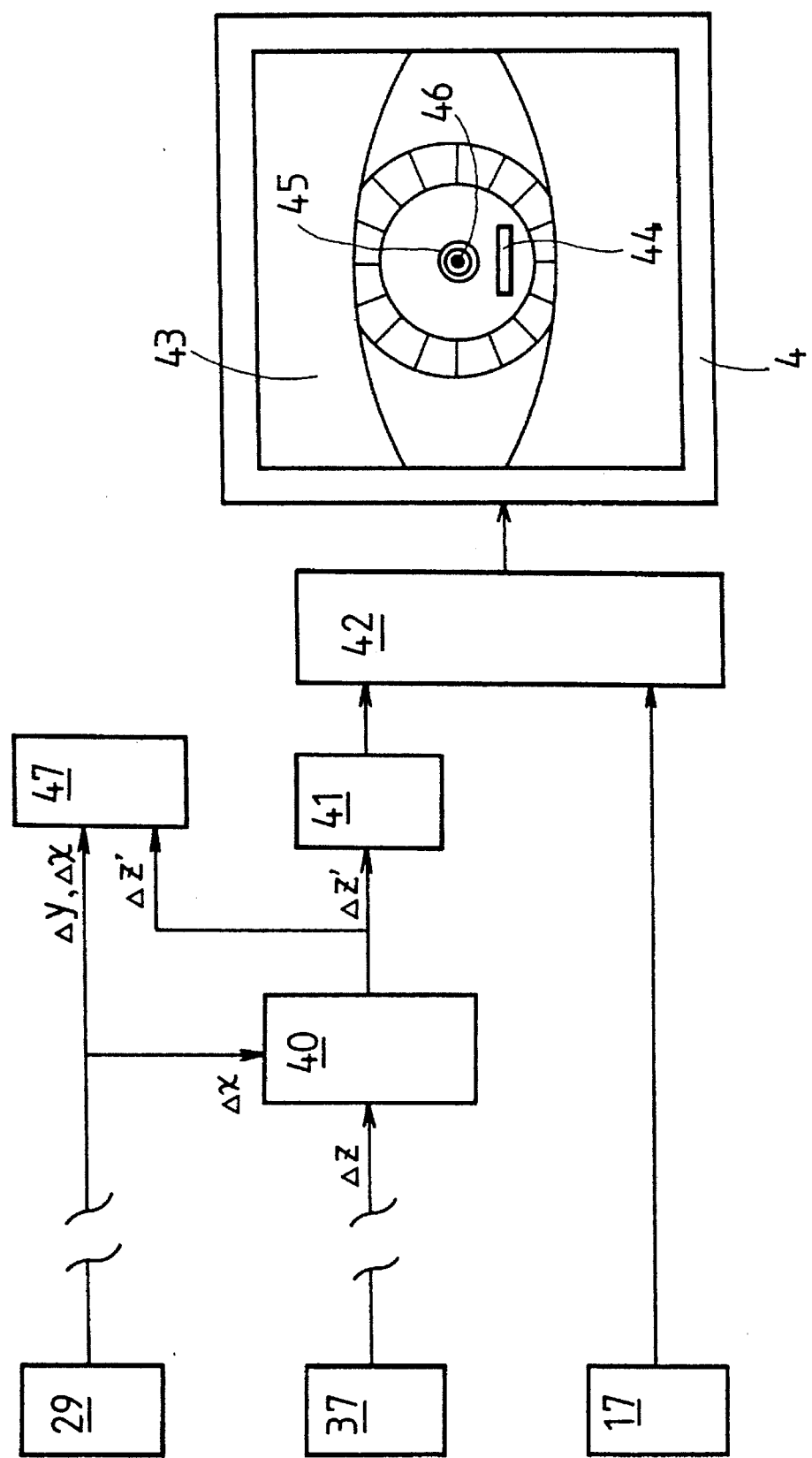
FIG. 3 is a block diagram of a signal processing system included in the intraocular pressure measuring apparatus of FIG. 1.

Referring to FIG. 3 showing a signal processing system for processing the output signals of the position detecting devices 29 and 37, the signal processing system comprises an arithmetic circuit 40, a graphic data producing circuit 41, a signal synthesizing circuit 42 and a measuring system control circuit 47. A front image 43 of the eyeball E, a distance mark 44, an image 45 of the reticle, an image 46 of the front index and so on are displayed on the monitor display 4. A signal processing unit, not shown, processes electric signals provided by the two-dimensional position detecting device 29 and the linear position detecting device 37 to provide signals representing the displacements Δ x, Δ y and Δ z. The signals representing the displacements Δ x and Δ z are given to the arithmetic circuit 40. When Δ x=0, the displacement Δ z represent the distance between the cornea Ec and the nozzle 12 correctly. When the optical observation system 11 is disposed obliquely to the eyeball E, Δ x ≠0, the displacement Δ z includes errors and the displacement Δ x must be corrected. The arithmetic circuit 40 calculates a distance information Δ z' corresponding to the distance between the cornea Ec and the nozzle 12 by using the following expression.

Δ z'=Δ z+k. Δ x where k=−(β2/β1)×cos θ is a constant, β1 is the lateral magnification of the optical front index detecting system 27, β2 is the lateral magnification of the optical distance index detecting system 33 and θ is the angle between the optical axes L and M and between the optical axes L and N.

Then, the graphic data producing circuit 41 produces a graphic signal representing the distance mark 44, and a position signal representing the position of the distance mark 44 on the screen of the monitor display 4. The synthesizing circuit 42 synthesizes video signals provided by the TV camera 17 and including the front image 43 of the eyeball E, the image 45 of the reticle and the image 46 of the front index, and the distance mark 44, and gives a synthetic signal to the monitor display 4. The distance mark 44 moves up and down relative to the image 45 of the reticle in a real time mode according to the variation of the distance between the cornea Ec and the nozzle 12. The distance mark 44 coincides with the image 45 of the reticle when the cornea Ec is at an appropriate distance from the nozzle 12.

The measuring system control circuit 47 receives the signals representing the displacements Δ x and Δ y, from the two-dimensional position detecting devices 29 and 37, and the signal representing the distance information Δ z' from the arithmetic circuit 40, examines the same signals to see if Δ x, Δ y and Δ z' are within predetermined ranges, respectively, and drives the measuring system, not shown, for measurement.

An operation for aligning the eyeball E and the noncontact intraocular pressure measuring apparatus will be described with reference to FIGS. 4(A), 4(B), 4(C) and 4(D) showing pictures displayed on the screen of the monitor display 4. The operating lever 3 is operated to align the center of the front image 43 of the eyeball E, i.e., the center of the pupil or the iris, and the image 45 of the reticle roughly for the adjustment of the vertical and horizontal positions of the eyeball E relative to the noncontact intraocular pressure measuring apparatus and for distance adjustment to focus the image of the eyeball E (FIG. 4(A)). When the cornea Ec is located in front of the nozzle 12, the image 46 of the front index and the distance mark 44 appears on the screen. Then, the operating lever is operated to bring the image 46 of the front index and the distance mark 44 into alignment with the image 45 of the reticle. When the vertical and horizontal positions of the eyeball E is adjusted correctly, the image 46 of the front index coincides with the image 45 of the reticle.

Figure 4:
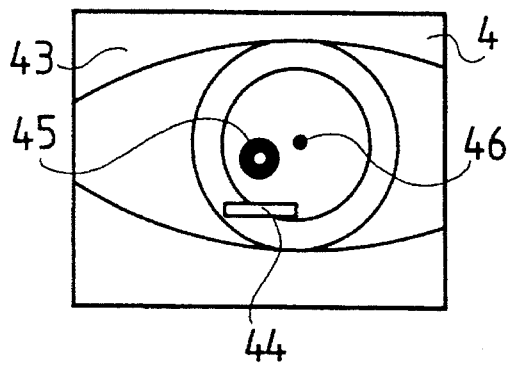
FIGS. 4(A), 4(B), 4(C) and 4(D) are pictorial views of assistance in explaining an intraocular pressure measuring apparatus aligning operation.
Figure 4:
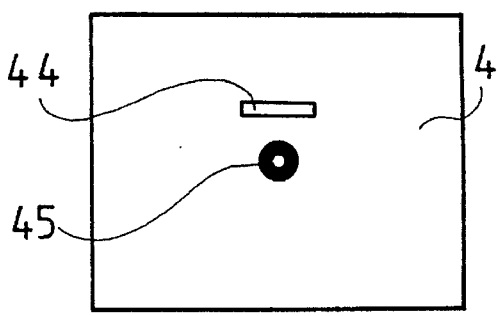
Figure 4:
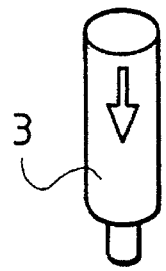
Figure 4:
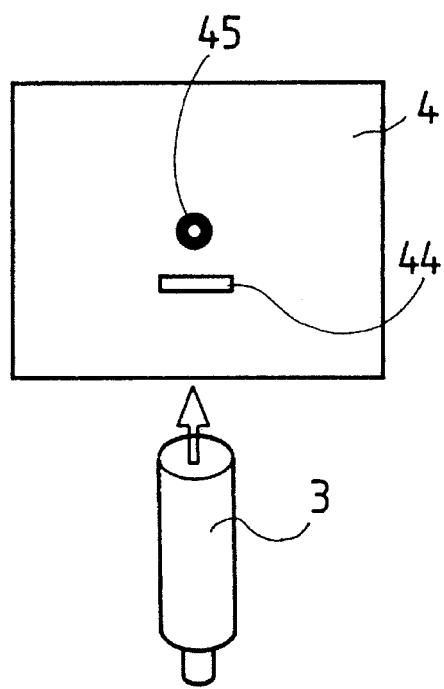
Figure 4:
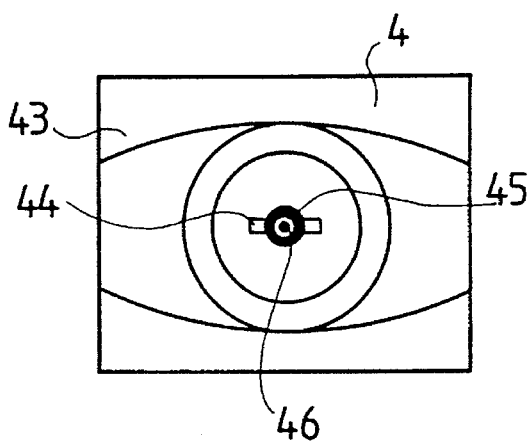

The distance mark 44 is displayed above the image 45 of the reticle as shown in FIG. 4(B) or below the image 45 of the reticle as shown in FIG. 4(C). When the distance between the cornea Ec and the nozzle 12 is shorter (longer) than the predetermined operating distance, the distance mark 44 appears above (below) the image 45 of the reticle. The distance between the distance mark 44 and the image 45 of the reticle corresponds to the difference between the actual operating distance and the predetermined operating distance. The operating lever 3 is tilted in the direction of the arrow in FIG. 4(B) or in the direction of the arrow in FIG. 4(C) to make the distance mark 44 coincide with the image 45 of the reticle as shown in FIG. 4(D).

After the eyeball E and the noncontact intraocular pressure measuring apparatus have thus been aligned, push-button of a measurement start switch, not shown, is depressed by the operator to start the measuring operation or the measuring system control circuit 47 starts the measuring operation automatically.

A two-dimensional position detecting device may be used instead of the linear position detecting device 37 to detect the vertical and horizontal positions of the eyeball E relative to the noncontact intraocular pressure measuring apparatus. Although part of the light flux representing the index formed by the optical front index projecting system is transmitted to the TV camera 17, the mark may be produced electrically on the basis of the output signal of the two-dimensional position detecting device 29.

As is apparent from the foregoing description, the ophthalmometric apparatus in accordance with the present invention enables the accurate adjustment of the distance between the eyeball and the ophthalmometric apparatus, quick, easy alignment of the eyeball and the ophthalmometric apparatus, and accurate adjustment of the three-dimensional position of the eyeball relative to the ophthalmometric apparatus.

Although the invention has been described in its preferred form with a certain degree of particularity, obviously many changes and variations are possible therein. It is therefore to be understood that the present invention may be practiced otherwise than as specifically described herein without departing from the scope and spirit thereof.

What is claimed is:

1. An ophthalmometric apparatus comprising an eyeball observing means for observing the front part of the eyeball, a measuring means, and a measuring means moving means for moving the measuring means relative to the eyeball;

the improvement comprising:

a first optical index forming system that projects a light beam along the optical axis of the eyeball observing means to form a first alignment index in the eyeball;

a first optical index detecting system that detects the position of the first alignment index on the basis of the light that travels along the optical axis of the eyeball observing means;

a second optical index forming system that projects a light beam on the eyeball along an optical axis inclined at an angle to the optical axis of the eyeball observing means to form a second alignment index in the eyeball;

a second optical index detecting system that detects the position of the second alignment index and has an optical axis in a substantially mirror image relation with the optical axis of the second optical index forming system with respect to the optical axis of the eyeball observing means;

a correction calculating means that calculates distance information about the distance between the eyeball and the eyeball observing means represented by the output of the second optical index detecting system, on the basis of the output of the first optical index detecting system; and a display means that displays distance information provided by the correction calculating means and representing the distance between the eyeball and the eyeball observing means in the observation field of the eyeball observing means.

2. The ophthalmometric apparatus according to claim 1, further comprising a processing means that processes the output detection signal of the first optical index detecting system and/or that of the second optical index detecting system to obtain position information about the vertical and horizontal positions of the eyeball relative to the eyeball observing means, wherein the first optical index detecting system is provided with a first position detector for detecting the position of the first alignment index, the second optical index detecting system is provided with a second position detector for detecting the position of the second alignment index, and at least either the first position detector or the second position detector is a two-dimensional position detecting device.

3. The ophthalmometric apparatus according to claim 2, wherein the first position detector of the first optical index detecting system is a two-dimensional position detector, and the second position detector of the second optical index detecting system is a linear position detector.

4. The ophthalmometric apparatus according to claim 1, wherein the correction calculating means calculates distance information about the distance between the eyeball and the eyeball observing means by using:

$$\Delta z' = \Delta z + k \cdot \Delta x, \quad k = -(\beta_2/\beta_1) \times \cos\theta$$

where $\Delta z'$ is distance information, k is a constant, $\beta_1$ is the lateral magnification of the first optical index detecting system, $\beta_2$ is the lateral magnification of the second optical index detecting system and $\theta$ is the angle between the optical axis of the eyeball observing means and that of the second optical index forming system.

5. The ophthalmometric apparatus according to claim 1, wherein the eyeball observing means is provided with a camera and a monitor display, and the display means is provided with a mark producing means for producing a mark indicating a direction in which the eyeball observing means is to be shifted relative to the eyeball and a distance for which the eyeball observing means is to be shifted relative to the eyeball.

6. The ophthalmometric apparatus according to claim 5, wherein the mark produced by the mark producing means is displayed on the monitor display at a position above a predetermined reference point and at a distance corresponding to the difference between a correct distance and an actual distance between the eyeball and the eyeball observing means from the reference point when the eyeball observing means is excessively close to the eyeball, and the mark is displayed on the monitor display at a position below the reference point and at a distance corresponding to the difference between a correct distance and an actual distance between the eyeball and the eyeball observing means from the reference point when the eyeball observing means is excessively far from the eyeball.

7. The ophthalmometric apparatus according to claim 1, wherein a light beam representing the first index is guided toward the eyeball observing means and the first optical index detecting system by a beam splitter disposed on the observation light path of the eyeball observing means.

8. An ophthalmometric apparatus comprising an optical alignment system and an eyeball observing means, the improvement comprising:

an optical front index projecting system for projecting a front index light beam for detecting the vertical and horizontal deviations of the eyeball from a correct position relative to the eyeball observing means on the eyeball from a position in front of the eyeball;

an optical front index detecting system that detects the front index light beam projected on the eyeball by the optical front index projecting system and reflected by the eyeball to determine the horizontal deviation $\Delta x$ of the eyeball from the correct position;

an optical distance index projecting system that projects a distance index light beam for detecting the difference between a correct distance and an actual distance between the eyeball and the eyeball observing means on the eyeball from a position obliquely in front of the eyeball;

an optical distance index detecting system that detects the distance index light beam reflected by the eyeball and determines the distance difference $\Delta z$ between the correct distance and the actual distance between the eyeball and the eyeball observing means; and a distance correction calculating means that calculates distance information for correcting the distance difference $\Delta z$ determined by the optical distance index detecting system, taking into consideration the horizontal deviation $\Delta x$ determined by the optical front index detecting system.

9. The ophthalmometric apparatus according to claim 8, further comprising a processing means that processes the output detection signal of the optical front index detecting system and/or that of the optical distance index detecting system, wherein at least either the position detector of the optical front index detecting system or the position detector of the optical distance index detecting system is a two-dimensional position detector.

10. The ophthalmometric apparatus according to claim 9, wherein the position detector of the optical front index detecting system is a two-dimensional position detector, and the position detector of the optical distance index detecting system is a linear position detector.

11. The ophthalmometric apparatus according to claim 8, wherein the distance correction calculating means calculates distance information about the distance between the eyeball and the eyeball observing means by using:

$$\Delta z' = \Delta z + k \cdot \Delta x, \quad k = -(\beta 2/\beta 1) \times \cos\theta$$

where $\Delta z'$ is distance information, k is a constant, $\beta 1$ is the lateral magnification of the optical front index detecting system, $\beta 2$ is the lateral magnification of the optical distance index detecting system, and $\theta$ is the angle between the optical axes of the optical front index projecting system and the optical distance index detecting system.

12. An ophthalmometric apparatus provided with an optical alignment system, comprising:

an optical observation system that takes a picture of the front part of the eyeball by a TV camera for observation;

an optical reticle image projecting system that projects an image of a reticle on the TV camera;

an optical front index projecting and observing system that projects a front index light beam representing a front index for vertical and horizontal deviations of the eyeball from a correct position on the eyeball from a position in front of the eyeball, and focuses the front index light beam reflected by the eyeball on the TV camera;

an optical front index detecting system optically connected to the optical front index projecting and observing system to detect part of the front index light beam projected on and reflected by the eyeball and to determine a horizontal deviation $\Delta x$ and a vertical deviation $\Delta y$ of the eyeball from the correct position;

an optical distance index projecting system that projects a distance index light beam representing a distance index for detecting the difference between the actual distance and the correct distance of the eyeball from the optical observation system from a position obliquely in front of the eyeball;

an optical distance index detecting system that detects the distance index light beam projected on and reflected by the eyeball to determine the difference $\Delta z$ between the actual distance and the correct distance of the eyeball from the optical observation system; and a distance correction calculating means that calculates a correction for correcting the difference $\Delta z$ determined by the optical distance detecting system, taking into consideration the horizontal deviation $\Delta x$.

13. The ophthalmometric apparatus according to claim 12, further comprising a processing means that processes the output detection signal of the optical front index detecting system and/or that of the optical distance index detecting system to obtain position information about the vertical and horizontal positions of the eyeball relative to the optical observation system, wherein at least either the position detector of the optical front index detecting system or that of the optical distance index detecting system is a two-dimensional position detector.

14. The ophthalmometric apparatus according to claim 12, wherein the position detector of the optical front index detecting system is a two-dimensional position detector, and the position detector of the optical distance index detecting system is a linear position detector.

15. The ophthalmometric apparatus according to claim 12, wherein the distance correction calculating means calculates a correction for correcting the distance difference $\Delta z$ determined by the optical distance index detecting system by using:

$$\Delta z' = \Delta z + k \cdot \Delta x, \quad k = -(\beta 2/\beta 1) \times \cos\theta$$

where $\Delta z'$ is a distance correction, k is a constant, $\Delta x$ is a horizontal deviation of the eyeball from the correct position, $\beta 1$ is the lateral magnification of the optical front index detecting system, $\beta 2$ is the lateral magnification of the optical distance index detecting system and $\theta$ is the angle of incidence of the distance index light beam on the eyeball.

16. The ophthalmometric apparatus according to claim 12 wherein the optical observation system is provided with a camera for taking a picture of the front part of the eyeball, and a display means for displaying an image of the front part of the eyeball taken by the camera, and the display means is provided with a mark producing means for producing a mark indicating a direction in which the optical observation system is to be shifted relative to the eyeball and a distance for which the optical observation system is to be shifted relative to the eyeball.

17. The ophthalmometric apparatus according to claim 16, wherein the mark produced by the mark producing means is displayed on the display means at a position above a predetermined reference point and at a distance corresponding to the difference between a correct distance and an actual distance between the eyeball and the optical observation system from the reference point when the optical observation system is excessively close to the eyeball, and the mark is displayed on the display means at a position below the reference point and at a distance corresponding to the difference between a correct distance and an actual distance between the eyeball and the optical observation system from the reference point when the optical observation system is excessively far from the eyeball.

* * * * *